(12) United States Patent
Talkachova (10) Patent No.: US 9,974,962 B2
(45) Date of Patent: May 22, 2018

(54) ALTERNANS PREVENTION AND TERMINATION

(71) Applicant: Regents of the University of Minnesota, Minneapolis, MN (US)

(72) Inventor: Alena Talkachova, Shoreview, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 241 days.

(21) Appl. No.: 14/695,593

(22) Filed: Apr. 24, 2015

(65) Prior Publication Data

US 2015/0314128 A1 Nov. 5, 2015

Related U.S. Application Data

(60) Provisional application No. 61/986,979, filed on May 1, 2014.

(51) Int. Cl.

| | | |
|---|---|---|
| *A61N 1/00* | (2006.01) | |
| *A61N 1/362* | (2006.01) | |
| *A61N 1/365* | (2006.01) | |
| *A61N 1/02* | (2006.01) | |
| *A61B 5/024* | (2006.01) | |
| *A61B 5/0245* | (2006.01) | |
| *A61B 5/04* | (2006.01) | |
| *A61B 5/0452* | (2006.01) | |

(52) U.S. Cl.
CPC .......... *A61N 1/3627* (2013.01); *A61B 5/0245* (2013.01); *A61B 5/02405* (2013.01); *A61B 5/04012* (2013.01); *A61N 1/025* (2013.01); *A61N 1/36507* (2013.01); *A61N 1/36514* (2013.01); *A61N 1/36592* (2013.01); *A61B 5/0452* (2013.01)

(58) Field of Classification Search
CPC .............................. A61N 1/3627; A61N 1/025
USPC ........................................................... 607/17
See application file for complete search history.

(56) References Cited

U.S. PATENT DOCUMENTS

| | | |
|---|---|---|
| 5,447,520 A | 9/1995 | Spano et al. |
| 5,836,974 A | 11/1998 | Christini et al. |
| | (Continued) | |

FOREIGN PATENT DOCUMENTS

EP 0450450 B1 7/1995

OTHER PUBLICATIONS

Stephen Duncan McIntyre: "Understanding and analyzing APD alternans", A Thesis Submitted to the Faculty of the Graduate School of the University of Minnesota, Oct. 2015.
(Continued)

*Primary Examiner* — Nadia A Mahmood
(74) *Attorney, Agent, or Firm* — Brian D. Kaul; Westman, Champlin & Koehler, P.A.

(57) ABSTRACT

In a method of preventing the formation of alternans in the heart of a patient, the heart is paced to control the TR interval of each heartbeat. The method may be performed using a heart monitoring and pacing device that includes a processor, memory, an electrocardiogram (ECG) sensing circuit, and a pulse generator. In the method, a heartbeat rate of the heart is detected and comparted to a threshold value stored in the memory. The heart is paced using the pulse generator to force the TR period of a limited number of heartbeats toward a targeted TR period, which is stored in the memory.

16 Claims, 9 Drawing Sheets

(56) References Cited

U.S. PATENT DOCUMENTS

| | | | |
|---|---|---|---|
| 5,928,271 | A | 7/1999 | Hess et al. |
| 7,818,055 | B2 | 10/2010 | Gilmour, Jr. et al. |
| 8,412,321 | B2 | 4/2013 | Gilmour, Jr. et al. |
| 8,565,876 | B2 | 10/2013 | Armoundas et al. |
| 8,620,414 | B2 | 12/2013 | Ghanem et al. |
| 8,634,903 | B2 | 1/2014 | Sharma et al. |
| 2003/0233132 | A1* | 12/2003 | Pastore .................. A61N 1/365 607/17 |
| 2013/0030313 | A1 | 1/2013 | Qu et al. |

OTHER PUBLICATIONS

Alena Talkachova: "Spatio-temporal formation and prediction of alternans in the heart", Biomedical Engineering Department of the University of Minnesota PowerPoint Presentation for Medtronic Technical Forum, Mar. 2013.

Armoundas AA, et al: A novel pacing method to suppress repolarization alternans in vivo: implications for arrhythmia prevention. Heart Rhythm. Apr. 2013;10(4):562-72. Doi: 10.1016/j.hrthm.2012.12.026. Epub Dec. 28, 2012.

Fox, J.J., Gilmour Jr., R.F., and Bodenschatz, E., 2002. "Conduction block in one-dimensional heart fiber", Phys. Rev. Lett., 89, p. 198101.

Fox, J.J., Bodenschatz, E., and Gilmour Jr., R. F., 2002. "Period-doubling instability and memory in cardiac tissue", Phys. Rev. Lett., 89, p. 138101.

Malik, M., and Camm, A. J., 1995, "Heart rate variability", Armonk, N.Y.: Futura Pub. Co.

E. G. Talkacheva, X. Zhao, "Nonlinear dynamics of periodically paced cardiac tissue", Nonlinear Dynamics, 68:3, 2012.

Simantirakis, E. et al.: "Novel Pacing Algorithms: Do They Represent a Beneficial Proposition for Patients, Physicians, and the Health Care System?" Eurospace. 2009;11(10)1272-1280.

Sridhar, S. et al; Suppression of Cardiac Alternans by Alternating-Period-Feedback Stimulations, Physical Review 87, 042712 (2013).

Srinivasan V. Narayanan and John W. Cain. Analysis of a Modified Feedback Control Technique for Suppressing Electrical Alternans in Cardiac Tissue. Morehead Electronic Journal of Applicable Mathematics, vol. 5 (2007), pp. 1-17.

E.G. Tolkacheva, M.M. Romeo, M. Guerraty, D.J. Gauthier; "Condition for alternans and its control in two-dimensional mapping model of paced cardiac tissue", Phys. Rev. E. v.69, p. 031904, 2004.

Tolkacheva, E.G., Schaeffer, D.G., Gauthier, D.J., and Krassowska, W. 2003. Condition for alternans and stability of the 1:1 response pattern in a "memory" model of paced cardiac dynamics. Phys. Rev. E. 67, p. 031904.

Watanabe, M. A., Otani, N. F., and Gilmour, Jr. R. F. 1995. "Biphasic restitution of action potential duration and complex dynamics in ventricular myocardium", Circ. Res., 76, p. 915.

Watanabe, M. A., and Koller, M. L., 2002. "Mathematical analysis of dynamics of cardiac memory and accommodation: theory and experiment", Am. J. Phys., 282, p. H1534.

Zipes, D. P. and Wellens, H. J., 1998. "Sudden cardiac death", Circulation, 98, pp. 2334-2351.

Banville, I., and Gray, R.A., 2002. "Effect of action potential duration and conduction velocity restitution and their spatial dispersion on alternans and the stability of arrhythmias", J. Cardiovasc. Electrophysiol. 13, p. 1141.

Franz, M.R. 2003. "The electrical restitution curve revisited: steep or flat slope—which is better?", J. Cardiovasc. Electrophys. 14:140-147.

Gilmour, Jr, R. F., 2002. "Electrical restitution and ventricular fibrillation: negotiating a slippery slope", J. Cardiovasc. Electrophysiol. 13, p. 1150.

Gilmour Jr., R. F., Otani, N. F., and Watanabe, M. A., 1997. "Memory and complex dynamics in cardiac Purkinje fibers", Am. J. Phys., 272, p. H1826.

Guevara, M., Ward, G., Shrier, A., and Glass, L., 1984. Computers in Cardiology, IEEE Computer Society, Silver Spring, MD, p. 167.

S. S. Kalb, E.G. Tolkacheva, D.G. Schaeffer, D.J. Glauthier, W. Krassowska; "Restitution in mapping models with an arbitrary amount of memory", Chaos v. 15, p. 023701, 2005.

Karma, A., 1994. "Electrical alternans and spiral wave breakup in cardiac tissue", Chaos, 4, p. 461.

Kleiger, R.E., Miller, J. P., Bigger, J.T., and Moss, A.J., 1987. "Decreased heart rate variability and its association with increased mortality after acute myocardial infarction", Am. J. Cardiol. 59, p. 256.

McIntyre, S.D., et al.: "The Effect of Feedback on Alternans Formation in the Heart", ASME 2012 5th Annual Dynamic Systems and Control Conference joint with the JSME 2012 11th Motion and Vibration Conference, Oct. 17-19, 2012, Fort Lauderdale, Florida, USA.

Otani, N.F., and Gilmour Jr., R. F., 1997. "Memory models for the electrical properties of local cardiac systems", J. Theor. Biol., 187, p. 409.

Cherry, E.M., Fenton, F.H. 2004 Suppression of alternans and conduction blocks despite APD restitution:electronic memory and conduction velocity effects. Am. J. Physiol. 286, pp. H2332-H2341.

Dai, S., & Keener, JP, 2012, "Using noise to determine cardiac restitution with memory". Physical Review E, 85(6), 061902.

Fenton, F.H., Cherry, E. M., Hastings H. M., and Evans, S. J., 2002. "Multiple mechanisms of spiral wave breakup in a model of cardiac electrical activity", Chaos, 12, p. 852.

Fox JJ, McHarg JL, Gilmour RF Jr. "Ionic mechanism of electrical alternans" Am. J. Phys., 282, p. H516, 2002.

Gilmour, Jr. R.F., and Chialvo, D. R., 1999. "Editorial: Electrical restitution, critical mass and the riddle of fibrillation", J. Cardiovasc. Electrophysical. 10, p. 1087.

Goldberger, A. L., Amaral, L. A. N., and Glass, L. 2000. "PhysioBank, PhysioToolkit, and PhysioNet: Components of a New Research Resource for Complex Physiologic Signals," Circulation, 101, p. e215-e220.

Hall, G. M., and Gauthier, D. J., 1999. "Experimental control of cardiac muscle alternans", Physc. Rev. Lett. 82, p. 2995.

Iravanian, S. et al.: "A Class of Monte-Carlo-Based Statistical Algorithms for Efficient Detection of Repolarization Alternans", IEEE Trans Biomed Eng. Jul. 2012; 59(7): 1882-1891. doi:10.1109/TBME.2012.2192733.

Dorenkamp, M. et al.: "T-Wave Alternans Testing in Pacemaker Patients: Comparison of Pacing Modes and Long-Term Prognostic Relevance", Pace, vol. 34, Sep. 2011, pp. 1054-1062. doi:10.1111/j.1540-8159.2011.03101.x.

S.S. Kalb, H. Dobrovolny, E.G. Tolkacheva, S.F. Idriss, W. Krassowska, D.J. Gauthier, "The restitution portrait: a new method for investigating rate-dependence restitution", J. Cardiovasc. Electrophysical., v. 15, N6, p. 698, 2004.

Koller, M. L., Riccio, M. L., and Gilmour, Jr., R. F., 1998. "Dynamic restitution of action potential duration during electrical alternans and ventricular fibrillation", Am. J. Physiol. 275, p. H1635.

La Rovere, M.T., Pinna G.D., et al., 2003, "Short-term heart rate variability strongly predicts sudden cardiac death in chronic heart failure patients", Circulation 107, p. 565.

Stephen D. McIntyre, Virenda Kakade, Yoichiro Mori, Elena G. Tolkacheva, Heart Rate Variability and Alternans Formation in the Heart: The Role of Feedback in Cardiac Dynamics, Journal of Theoretical Biology, http://dx.doi.org/10.1016/j.jtbi.2014.02.015.

Myerburg, R. J., and Spooner, P. M., 2001. "Opportunities for sudden death prevention:directions for new clinical and basic research", Cardiovasc Res. 50, pp. 177-185.

Nolasco, J. B., and Dahlen, R. W., 1968. "A graphic method for the study of alternation in cardiac action potentials", J. Appl. Physiol., 25, p. 191.

Qu, Z.: "Controlling Cardiac Alternans", Heart Rhythm, vol. 10, No. 4, Apr. 2013, pp. 573-574. University of California, Los Angeles, CA.

Riccio, M. L, Koller, M. L., and Gilmour, Jr., R. F., 1999. "Electrical restitution and spatiotemporal organization during ventricular fibrillation", Circ. Res. 84, p. 955.

Sayadi O., Merchant F.M., Puppala D., Mela T., Singh J.P., Heist E.K., Owen C., Armoundas A.A. A Novel Method for Determining the Phase of T-Wave Alternans: Diagnostic and Therapeutic Implications. Circ Arrhythm Electrophysiol. 2013;6:818-826, published online before print Jul. 24, 2013.

* cited by examiner

ALTERNANS PREVENTION AND TERMINATION

CROSS-REFERENCE TO RELATED APPLICATION

The present application is based on and claims the benefit of U.S. provisional patent application Ser. No. 61/986,979, filed May 1, 2014, the content of which is hereby incorporated by reference in its entirety.

This invention was made with government support under PHY-1255410 awarded by the National Science Foundation. The government has certain right in the invention.

BACKGROUND

Catastrophic heart rhythm disturbances are among the leading causes of death in the United States. The most dangerous of these disturbances is ventricular fibrillation, a disturbance in which disordered wave propagation causes a fatal disruption of the synchronous contraction of the ventricle. A beat-to-beat alternation in the action potential duration (APD) of myocytes, i.e. alternans, is believed to be a direct precursor of ventricular fibrillation in the whole heart.

A common approach for the prediction of alternans is to construct the restitution curve, which is the nonlinear functional relationship between the APD and the preceding diastolic interval (DI). It has been proposed that alternans appears when the magnitude of the slope of the restitution curve exceeds one, known as the restitution hypothesis. However, this restitution hypothesis was derived under the assumption of periodic stimulation, when there is a dependence of the DI on the immediate preceding APD (i.e. feedback). In addition, under physiological conditions, the heart rate exhibits substantial variations in time, known as heart rate variability (HRV), which introduces deviations from periodic stimulation in the system.

SUMMARY

Embodiments of the invention are directed to a method of preventing the formation of alternans in the heart of a patient. In some embodiments, of the method alternans are prevented from forming in the heart of a patient by pacing the heart to control the TR interval of each heartbeat.

In some embodiments of the method, a heart monitoring and pacing device is used. In some embodiments, the heart monitoring and pacing device includes a processor, memory, an electrocardiogram (ECG) sensing circuit, and a pulse generator. In some embodiments of the method, a heartbeat rate of the heart is detected using the ECG sensing circuit, or other suitable circuitry, and the processor. A determination is made using the processor that the detected heartbeat rate has reached a threshold value, which is stored in the memory. When the heartbeat rate has reached the threshold value, the heart is paced using the pulse generator to force the TR period of a limited number of heartbeats toward a targeted TR period, which is stored in the memory. This prevents the formation of alternans in the heart.

Additional embodiments of the method are directed to terminating alternans after they have formed in the heart. In some embodiments, the alternans are terminated by pacing the heart to control the TR interval of each heartbeat.

In some embodiments of the method of terminating alternans in the heart of a patient, a heart monitoring and pacing device is used. In some embodiments, the heart monitoring and pacing device includes a processor, memory, an ECG sensing circuit, and a pulse generator. In some embodiments of the method, alternans are detected in the heart by analyzing ECG traces corresponding to a plurality of heartbeats using the ECG sensing circuit and the processor. The TR period of a limited number of heartbeats is then controlled by applying heart pacing pulses to the heart at a forced TR period using the pulse generator. This leads to the termination of the alternans in the heart.

Other embodiments of the invention are directed to an implantable medical device that is used to perform embodiments of the methods described above. In some embodiments, the heart monitoring and pacing device includes a processor, memory, an ECG sensing circuit, and a pulse generator.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Embodiments of the invention are described more fully hereinafter with reference to the accompanying figures and tables. Elements that are identified using the same or similar reference characters refer to the same or similar elements. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Specific details are given in the following description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices. Such computer readable media and memory for computer programs and software do not include transitory waves or signals.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the invention may also be described using flowchart illustrations and block diagrams. Although a flowchart may describe the operations as a sequential process, many of the operations can be performed in parallel or concurrently. In addition, the order of the operations may be re-arranged. A process is terminated when its operations are completed, but could have additional steps not included in a figure or described herein.

It is understood that one or more of the blocks (of the flowcharts and block diagrams) may be implemented by computer program instructions. These program instructions may be provided to a processor circuit, such as a microprocessor, microcontroller or other processor, which executes the instructions to implement the functions specified in the block or blocks through a series of operational steps to be performed by the processor(s) and corresponding hardware components.

Embodiments of the invention are directed to the prevention of alternans formation. Initially, two deviations from the periodic pacing are described: (1) the absence of feedback, and (2) the presence of heart rate variability (HRV). The role of these two deviations from the periodic pacing on alternans formation in isolated cardiac myocytes using numerical simulations of an ionic model of the cardiac action potential will be described. This model is used with two different pacing protocols: a periodic pacing protocol with feedback and a protocol without feedback. The inventors have discovered that when HRV is incorporated in the periodic pacing protocol, it facilitated alternans formation in the isolated cell, but did not significantly change the magnitude of alternans. On the other hand, in the case of the pacing protocol without feedback, alternans formation was prevented, even in the presence of HRV.

One of the most fundamental characteristics of cardiac cells is the shortening of the action potential duration (APD) as the heart rate increases, a phenomenon known as electrical restitution. Restitution plays a vital role in heart function: for a given heart rate, a shorter APD allows for a longer diastolic interval (DI), thereby giving adequate time for the heart to refill with blood. Although important for life at moderate heart rates, at higher rates, restitution may result in life-threatening cardiac rhythms and ventricular fibrillation (VF), in particular.

It is generally believed that T-wave alternans, defined as an alternating change in the amplitude or shape of the T-wave in the electrocardiogram (ECG), is a precursor of cardiac electrical instability. T-wave alternans results from APD alternans at the cellular level. A common technique for studying the initiation and maintenance of alternans and other complex rhythms is to analyze the restitution curve, the nonlinear functional relationship between the APD and the preceding DI. While detailed ionic models were used extensively to study the response of cardiac myocytes to stimulation, mapping models were introduced to focus on restitution. Specifically, it was proposed that the APD could be determined as a function of the preceding DI, essentially forming the one-dimensional mapping model $$APD_{n+1} = f(DI_n). \tag{1}$$

Here, f is the restitution curve, $APD_{n+1}$ is the APD generated by the $(n+1)^{st}$ stimulus and $DI_n$ is the $n^{th}$ DI, i.e., the interval during which the tissue recovers to its resting state after the end of the previous ($n^{th}$) action potential.

In 1968, Nolasco and Dahlen (Nolasco, J. B., and Dahlen, R. W., 1968. "A graphic method for the study of alternation in cardiac action potentials", *J. Appl. Physiol.*, 25, p. 191.) developed a graphical method to analyze and predict APD alternans in a mapping model (1) under the assumption that pacing occurs at a constant rate, i.e. when the APD and DI are related through the pacing relation $$APD_n + DI_n = BCL_n, \tag{2}$$

where the basic cycle length $BCL_n$=BCL (a constant) under periodic pacing. Using Eqs. (1) and (2), it was proposed that the normal cardiac rhythm, or so-called 1:1 response, becomes unstable and alternans occurs when the magnitude of the slope of the restitution curve exceeds one, $$S_r = \left| \frac{df}{dDI} \right|_{DI=DI_n} = |f'| \geq 1, \tag{3}$$

known as the restitution hypothesis. This restitution hypothesis has been confirmed in some experiments and has led to the assumption that flattening the restitution curve will help prevent VF. However, recent experimental results have shown that this hypothesis is incorrect in many situations, where the normal cardiac rhythm is observed when the restitution curve is very steep or in which the transition to alternans occurs in the presence of a flat restitution curve.

One of the reasons why the restitution condition fails experimentally is that Nolasco and Dahlen's approach is valid only for periodic pacing, i.e. when $BCL_n$=BCL is a constant in Eq. (2), and cannot be applied for complex stimulation regimes, such as those which result in physiological heart rates that exhibit HRV. It is known that the heart rate is regulated by the autonomic nervous system, baroreceptors, and other factors. The sympathetic components of the autonomic nervous system increase heart rate by releasing the neural hormones catecholamine, epinephrine, and norepinephrine; while the parasympathetic components decrease heart rate through the releasing of the neurohormone acetylcholine. HRV is affected by, but not limited to, respiration, thermoregulation, hormonal regulation, blood pressure, etc. HRV is a temporal variation between sequences of consecutive heartbeats, which reflects the balance between sympathetic and parasympathetic mediators. HRV alters pacing relation Eq. (2), in which $BCL_n$ is no longer a constant, and therefore, might affect the overall dynamics of cardiac rhythm. Despite these important consequences, the effect of HRV on alternans formation in the heart has never been investigated.

The inventors have determined the roles of (1) absence of feedback, and (2) presence of HRV on alternans formation in isolated cardiac myocytes using numerical simulations of physiological ionic model of cardiac action potential. This was accomplished by separately analyzing ECG data from Healthy and Diseased patients to determine HRV, feedback, and several other important physiological parameters used to design pacing protocols for the numerical simulations. Two pacing protocols were designed: Protocol 1 with feedback and Protocol 2 without feedback. Both protocols were then used to investigate the influence of feedback and HRV on the formation of alternans in an ionic model of cardiac action potential.

HRV Data Analysis

ECG data analyses from 14 patients taken from Physionet database were performed. Based on the information provided in Physionet, the data sets were divided in two different categories: Healthy (n=8), and Diseased (n=6). All Diseased patients were diagnosed with myocardial infarction.

Figure 1:
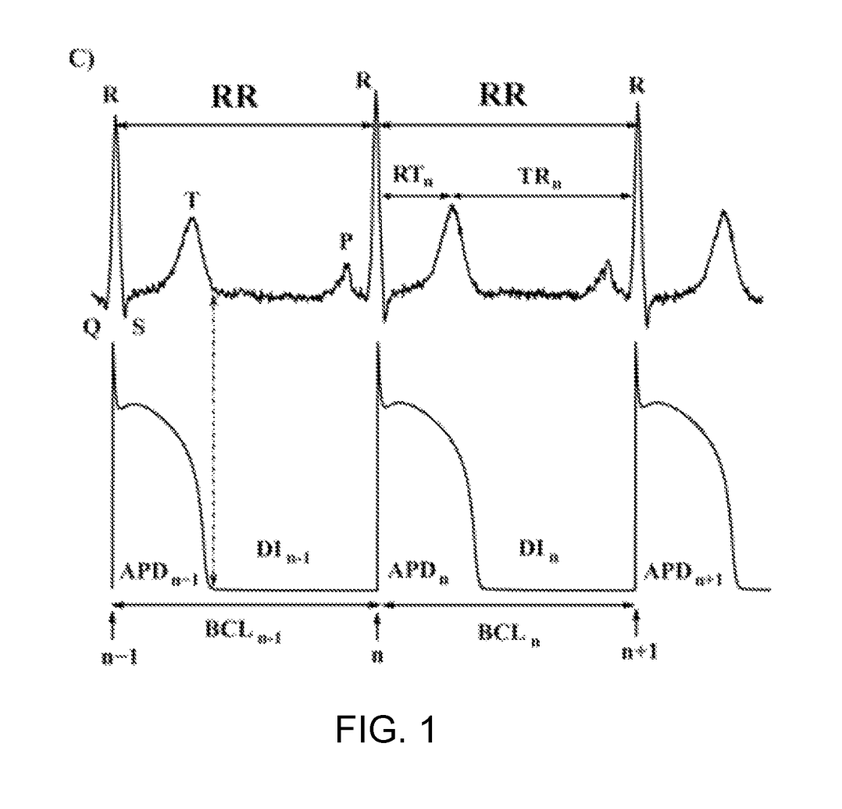
FIG. 1 is a graph illustrating the correspondence between the action potential duration (APD), diastolic interval (DI), and the basic cycle length (BCL) values and the RT, TR, and RR intervals from an electrocardiogram (ECG), respectively.

Each ECG trace was approximately 120 seconds long. We applied band-pass filtering to each data set, and calculated the following parameters: RR intervals, determined as a distance between RR peaks; standard deviation ($SD_{RR}$) and average ($AVG_{RR}$) of RR intervals; TR and RT intervals, determined as a time between T and R peaks, and R and T peaks within RR intervals. FIG. 1 shows a direct correspondence between APD, DI, and BCL values and the RT, TR, and RR intervals from the ECG, respectively.

HRV for each ECG data set was determined as $$HRV = \frac{SD_{RR}}{AVG_{RR}} * 100\%. \tag{4}$$

The sensitivity of each ECG data set, which is an indirect representation of feedback, was calculated using the following equation $$s = \frac{SD_{TR}}{AVG_{TR}} \frac{AVG_{RT}}{SD_{RT}}, \tag{5}$$

where $AVG_{TR}$ and $AVG_{RT}$ are the average TR and RT values from each ECG data set, respectively. All these parameters were calculated separately for Healthy and Diseased patients.

Numerical Simulations

To investigate the influences of feedback and HRV on alternans formation, we used a physiological ionic model of a canine cardiac action potential. This model exhibits APD alternans while being periodically paced at progressively decreased BCLs, and therefore, a distinct value of BCL for the onset of alternans, $BCL_{start}$, and for the end of alternans, $BCL_{end}$, can be defined. The system of ordinary differential equations was solved using a two-step Runge-Kutta method with a time step of $\Delta t$=0.05 ms. The APD was calculated at 80% repolarization.

Two different pacing protocols were used to model feedback and HRV in numerical simulations, based on ECG analysis: Protocol 1, a periodic pacing protocol with feedback, and Protocol 2, a pacing protocol without feedback. Specifically, the RR data from ECG data analysis was used for Protocol 1, and TR data was used for Protocol 2.

The periodic pacing protocol (Protocol 1) is described by Eq. (2), where $BCL_n$=BCL if HRV is absent. This pacing protocol entails a strong connection between $APD_n$ and $DI_n$ and thus possesses feedback associated with periodic pacing, as described in Section 1. We started pacing at BCL=400 ms, and then decreased BCL by increments of 10 ms down to 100 ms. 120 stimuli were applied at each BCL in order to reach steady state. HRV was modeled by modifying the $BCL_n$ in Eq. (2) to the following:

$$BCL_n \equiv BCL_{HRV} = BCL + \delta(HRV), \quad (6)$$

where δ(HRV) is a random number with a mean of zero and a standard deviation HRV*BCL, and HRV is defined by Eq. (4).

In the pacing protocol without feedback (Protocol 2), the connection between $APD_n$ and $DI_n$ was eliminated by fixing the $DI_n$ values. The DI values were set to correspond to the steady state values of DI from Protocol 1 with HRV=0% when 1:1 responses were present. When alternans was present in Protocol 1, we chose three different DI values: the high DI value, the low DI value and the DI value corresponding to the average of two consecutive stimuli. However, since the results of numerical simulations were similar for all three DI values, for demonstration purpose we chose to show results only for average DI values. Similar to Protocol 1, HRV was modeled as the following, $$DI_n \equiv DI_{HRV} = DI + \delta(HRV) \quad (7)$$

where δ(HRV) is a random number with a mean of zero and a standard deviation HRV*BCL, and HRV is defined by Eq. (4).

For both protocols, the value of HRV was varied from 0% to 6% to cover physiological range of HRV calculated from the ECG data, both for Healthy and Diseased patients. For each value of HRV, both protocols were run 10 times to mimic a stochastic process. The last 20 APD's for each BCL (or DI) for each run, representing steady state responses, were divided into even and odd beats and the mean values of $<APD>_{even}$ and $<APD>_{odd}$, and corresponding standard errors were calculated separately. For each run, alternans was defined as $$\Delta APD = |\langle APD \rangle_{even} - \langle APD \rangle_{odd}| \geq 5 \text{ ms}. \quad (8)$$

When HRV was present, we ensured that the magnitude of alternans is larger than the standard deviation of the mean BCL, to account for noise. Equation (8) was also used to determine the BCL at which alternans appears, $BCL_{start}$, and the BCL at which alternans ends, $BCL_{end}$, at each run. The mean $\langle BCL \rangle_{start}$ and $\langle BCL \rangle_{end}$ with their respective standard errors were then determined from the 10 runs. Once $BCL_{start}$ was determined at each run, a restitution curve was constructed from the last 20 APD and DI values taken from each BCL prior to the onset of alternans, $BCL_{start}$. The restitution curve was then fitted with an exponential function, and the slope of the restitution, $S_r^{max}$, was calculated at the mean DI value corresponding to the BCL value immediately preceding $BCL_{start}$. Note that $S_r^{max}$ represents the maximum slope of the restitution curve just prior the onset of alternans, i.e. during 1:1 behavior. The mean $<S_r^{max}>$ and the standard error were then determined from the 10 runs.

Statistical Analysis

Statistical significance of the ECG data, presented in Tables 1 and 2 below, was determined by one-way ANOVA analysis. Data was considered statistically significant if p<0.05. Statistical significance of numerical data was determined using Student's t-test. Numerical results were considered statistically significant if p<0.01.

TABLE 1

ECG Analysis of Healthy Patients representing average RR ($AVG_{RR}$), TR ($AVG_{TR}$) and RT ($AVG_{RT}$) intervals, standard deviations of the RR ($SD_{RR}$), TR ($SD_{TR}$) and RT ($SD_{RT}$) intervals, and corresponding HRVs.

| | RR | | | TR | | | RT | | |
|---|---|---|---|---|---|---|---|---|---|
| Patient ID | $AVG_{RR}$ (ms) | $SD_{RR}$ (ms) | $HRV_{RR}$ (%) | $AVG_{TR}$ (ms) | $SD_{TR}$ (ms) | $HRV_{TR}$ (%) | $AVG_{RT}$ (ms) | $SD_{RT}$ (ms) | $HRV_{RT}$ (%) |
| S0306 | 975.8 | 60.9 | 6.2 | 702.3 | 59.2 | 8.4 | 270.6 | 4.8 | 1.8 |
| S0303 | 771.5 | 34.5 | 4.5 | 533.6 | 34.4 | 6.5 | 239.9 | 3.0 | 1.2 |
| S0292 | 874.3 | 39.3 | 4.5 | 637.1 | 38.7 | 6.1 | 237.3 | 3.3 | 1.4 |
| S0304 | 888.9 | 22.6 | 2.5 | 592.6 | 23.0 | 3.9 | 296.4 | 3.3 | 1.1 |
| S0308 | 839.2 | 27.4 | 3.3 | 588.8 | 27.6 | 4.7 | 250.3 | 3.1 | 1.3 |
| S0452 | 1047.5 | 46.0 | 4.4 | 747.1 | 45.1 | 6.0 | 300.5 | 4.4 | 1.5 |
| S0457 | 1044.0 | 67.7 | 6.5 | 771.1 | 67.9 | 8.8 | 272.9 | 3.6 | 1.3 |
| S0460 | 1113.8 | 69.4 | 6.2 | 808.4 | 68.7 | 8.5 | 305.3 | 3.2 | 1.0 |
| AVG | 944.3 ± 42.1* | 46.0 ± 6.4* | 4.8 ± 1.5* | 672.4 ± 93.0*#$ | 45.6 ± 16.7*$ | 6.6 ± 1.7*#$ | 271.7 ± 25.6#$ | 3.6 ± 0.6*#$ | 1.3 ± 0.2*#$ |

*denotes statistical significance (p < 0.05) between Healthy and Diseased patients.
denotes statistical significance (p < 0.05) between RR and TR (RT) parameters within Healthy patients.
$denotes statistical significance (p < 0.05) between TR and RT parameters within Healthy patients.

TABLE 2

ECG Analysis of Diseased Patients representing average RR ($AVG_{RR}$), TR ($AVG_{TR}$) and RT ($AVG_{RT}$) intervals, standard deviations of the RR ($SD_{RR}$), TR ($SD_{TR}$) and RT ($SD_{RT}$) intervals, and corresponding HRVs.

| | RR | | | TR | | | RT | | |
|---|---|---|---|---|---|---|---|---|---|
| Patient ID | $AVG_{RR}$ (ms) | $SD_{RR}$ (ms) | $HRV_{RR}$ (%) | $AVG_{TR}$ (ms) | $SD_{TR}$ (ms) | $HRV_{TR}$ (%) | $AVG_{RT}$ (ms) | $SD_{RT}$ (ms) | $HRV_{RT}$ (%) |
| TWA18 | 699.7 | 19.6 | 2.8 | 441.2 | 19.8 | 4.5 | 258.4 | 9.3 | 3.6 |
| TWA38 | 711.7 | 18.5 | 2.6 | 464.3 | 18.8 | 4.1 | 247.5 | 3.2 | 1.3 |
| TWA31 | 710.0 | 13.8 | 1.9 | 454.2 | 14.2 | 3.1 | 256.1 | 6.2 | 2.4 |

TABLE 2-continued

ECG Analysis of Diseased Patients representing average RR ($AVG_{RR}$),
TR ($AVG_{TR}$) and RT ($AVG_{RT}$) intervals, standard deviations of the RR ($SD_{RR}$), TR
($SD_{TR}$) and RT ($SD_{RT}$) intervals, and corresponding HRVs.

| Patient ID | RR | | | TR | | | RT | | |
|---|---|---|---|---|---|---|---|---|---|
| | $AVG_{RR}$ (ms) | $SD_{RR}$ (ms) | $HRV_{RR}$ (%) | $AVG_{TR}$ (ms) | $SD_{TR}$ (ms) | $HRV_{TR}$ (%) | $AVG_{RT}$ (ms) | $SD_{RT}$ (ms) | $HRV_{RT}$ (%) |
| TWA11 | 786.0 | 20.8 | 2.6 | 538.4 | 20.5 | 3.8 | 247.9 | 4.2 | 1.7 |
| TWA20 | 814.8 | 25.7 | 3.2 | 571.4 | 25.5 | 4.5 | 243.4 | 4.0 | 1.6 |
| TWA42 | 824.0 | 34.5 | 4.2 | 557.6 | 34.5 | 6.2 | 266.4 | 6.1 | 2.3 |
| AVG | 757.2 ± 23.3* | 22.2 ± 2.9* | 2.9 ± 0.8* | 504.5 ± 52.6*#$ | 22.2 ± 6.4*$ | 4.4 ± 0.9*#$ | 253.3 ± 7.8*#$ | 5.5 ± 2.0*#$ | 2.2 ± 0.7*$ |

*denotes statistical significance (p < 0.05) between Healthy and Diseased patients.
denotes statistical significance (p < 0.05) between RR and TR (RT) parameters within Diseased patients.
$denotes statistical significance (p < 0.05) between TR and RT parameters within Diseased patients.

Results

1. The Role of Feedback in Alternans Formation: Analytical Insight

As mentioned in above, Eqs. (1) and (2) have been widely used to describe dynamics of cardiac myocytes subject to periodic pacing. Let us look at these equations a little closer, since we want to determine the behavior of the system near the 1:1 steady state value of Eq. (1).

Let APD* and DI* be the steady state values of Eq. (1), such that $$APD^* = f(BCL - APD^*) = f(DI^*). \quad (9)$$

Taking the difference between Eqs. (1) and (9), we can write $$APD_{n+1} - APD^* = f(DI_n) - f(DI^*). \quad (10)$$

We can approximate the right-hand side of Eq. (10) as the following:

$$f'(DI^*)(DI_n - DI^*) = S_r(DI_n - DI^*). \quad (11)$$

Therefore, combining Eqs. (10) and (11) we obtain $$(APD_{n+1} - APD^*) = S_r(DI_n - DI^*). \quad (12)$$

Equation (12) describes the restitution properties of the heart, suggesting that small changes in APD are proportional to small changes in preceding DI. It is important to note that Eq. (12) is linear, since $S_r$ is a constant for any given small changes, and therefore, cannot describe complex cardiac rhythms, such as alternans. The physiological basis for restitution properties of the heart, arising from, among other factors, incomplete recovery from inactivation of delayed rectifier ionic channels, has been discussed previously in greater details.

In the case of periodic pacing with constant BCL (pacing Protocol 1), the APD and DI are related through the pacing relation (2), which can be rewritten as $$DI_n = BCL - APD_n,$$

$$DI^* = BCL - APD^* \quad (13)$$

and therefore, the following relation can be derived:

$$APD_n - APD^* = -(DI_n - DI^*) \quad (14)$$

Equation (14) describes the feedback associated with periodic pacing protocol, and suggests that small changes in DI are proportional with opposite sign to small changes in APD.

Combination of the restitution properties of the myocytes (Eq. (12)) with the relationship derived based on periodic pacing (Eq. (14)) leads to a recurrence relation $$APD_{n+1} - APD^* = -S_r(APD_n - APD^*) \quad (15)$$

that has been used to describe different dynamical behavior of cardiac myocytes: 1:1 responses and possible presence of alternans. Indeed, for $|S_r| > 1$, any small changes in APD that appear after $n^{th}$ stimulus is applied, will enhance the difference $APD_{n+1} - APD^*$ during further pacing, i.e. at the next $(n+1)^{st}$ stimulus. If $|S_r| < 1$, relation (15) describes 1:1 responses, since small changes in APD will eventually die out.

In the case when the connection between $APD_n$ and $DI_n$ is eliminated by fixing the $DI_n$ value (pacing Protocol 2), Eq. (13) is no longer valid, so feedback is absent. Therefore, we cannot derive Eq. (15) and as a result are unable to mathematically explain the mechanism of alternans formation in isolated cells. Indeed, mapping model (1) will return a single $APD_{n+1}$ value for a fixed $DI_n$ in the absence of feedback.

Figure 2A:
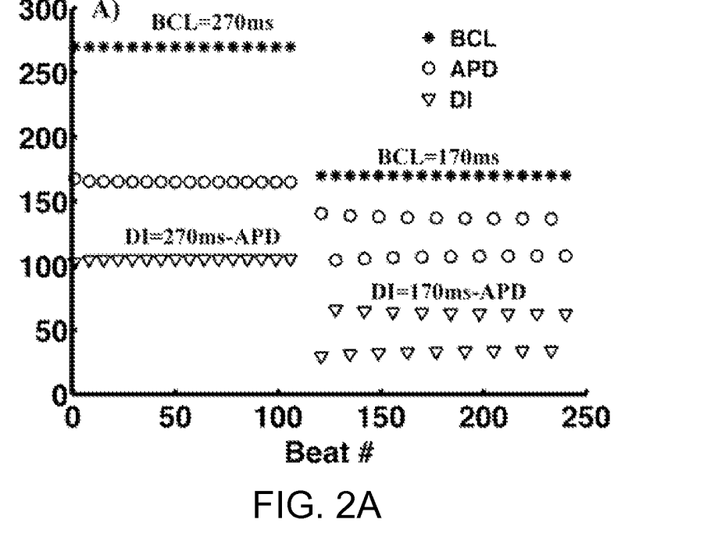
FIGS. 2A and 2B are charts illustrating BCL (stars), APD (open circles), and DI (open triangles) as a function of beat number respectively for embodiments of alternans treatment Protocols 1 and 2.
Figure 2B:
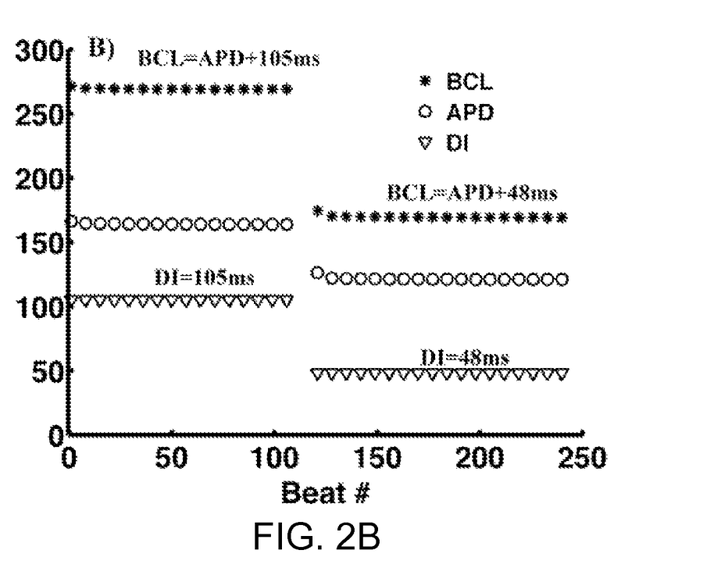

The difference between pacing protocols with and without feedback is illustrated in FIG. 2, where BCLs (stars), APDs (open circles), and DIs (open triangles) are shown for Protocol 1 (FIG. 2A) and Protocol 2 (FIG. 2B) as a function of beat number for the case of HRV=0%. For Protocol 1, the BCL was changed from 270 ms to 170 ms, and corresponding values of DI were calculated using Eq. (13). Note that the slope of the restitution curve $S_r > 1$ at BCL=170 ms, leading to the formation of alternans due to the presence of feedback (Eq. (14)), and therefore, recurrence relation (15). In contrast, no alternans is present in FIG. 2B, when DI is changed from 105 ms to 48 ms. Note, that the calculated values of BCLs are very similar to those from FIG. 2A.

2. ECG Data Analysis

Figure 3A:
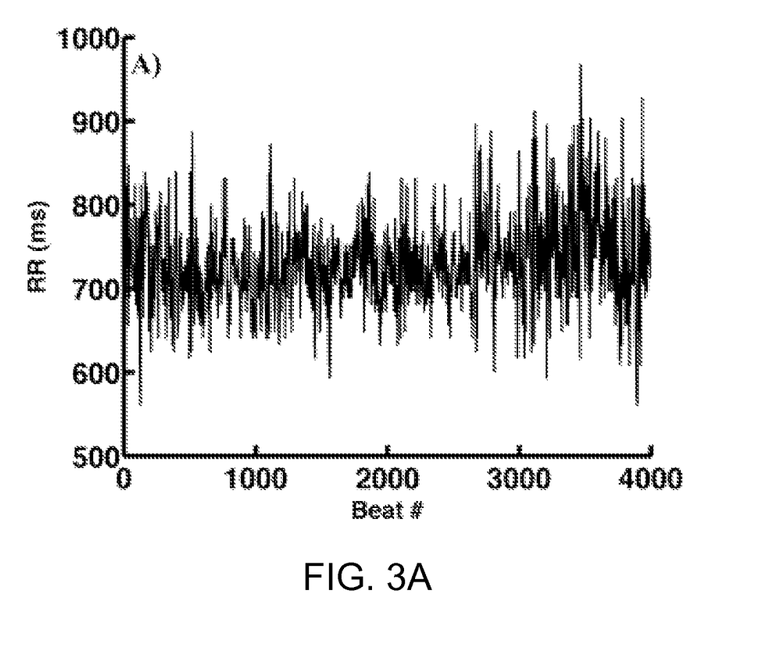
FIG. 3A is an exemplary ECG trace of a 32-year-old male with normal sinus rhythm
Figure 3B:
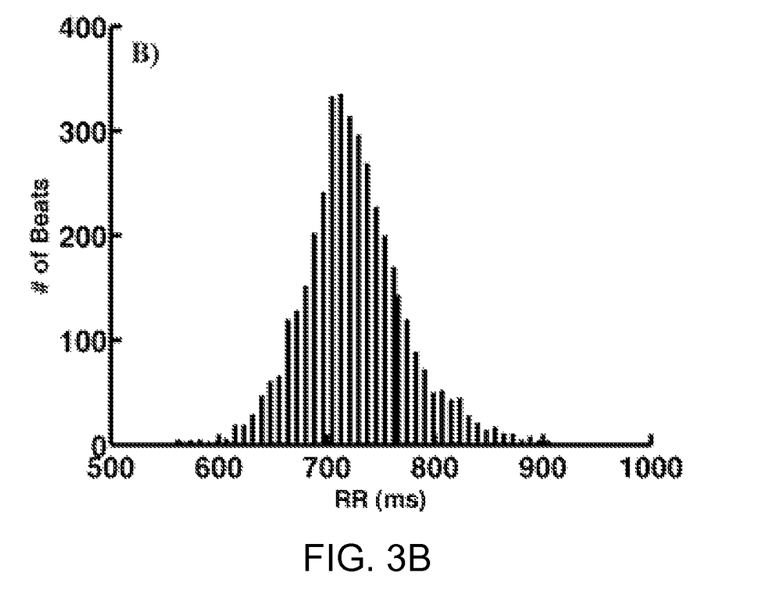
FIG. 3B is a histogram of the RR intervals calculated from the ECG trace shown in FIG. 3A.

FIG. 3A shows a representative example of RR intervals as a function of beat number taken from an ECG of a Healthy patient's data, illustrating the presence of HRV (Goldberger, A. L., Amaral, L. A. N., and Glass, L. 2000. "PhysioBank, PhysioToolkit, and PhysioNet: Components of a New Research Resource for Complex Physiologic Signals," Circulation, 101, p. e215-e220). FIG. 3B shows the histogram of RR intervals from the data in FIG. 3A. Note the approximately normal distribution of RR intervals in FIG. 3B. Both Healthy and Diseased patients' RR distributions were qualitatively similar to the one shown in FIG. 1, and therefore we chose a normal distribution for the random numbers in Eqs. (6) and (7). FIG. 1 illustrates the relationship of the RR, RT, and TR intervals to the BCL, APD, and DI respectively.

Comprehensive analyses of ECG traces from the two groups of patients, Healthy and Diseased, are presented in Table 1 and Table 2, respectively. Note that $AVG_{RR}$, (944.38±42.08 ms vs. 757.7±23.25 ms, p<0.05), $SD_{RR}$, (45.98±6.42 ms vs. 22.15±2.92 ms, p<0.01), and HRV (4.76±1.45% vs. 2.89±0.75%, p<0.05) are significantly larger for Healthy patients in comparison with Diseased patients.

Figure 4A:
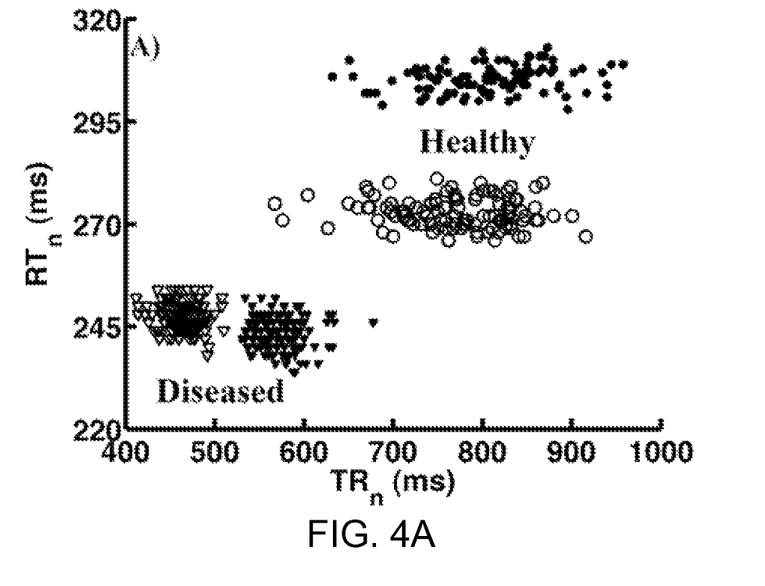
FIG. 4A is an exemplary representative plot of RT vs. TR intervals for two Healthy (circles) and two Diseased (triangles) patients.
Figure 4B:
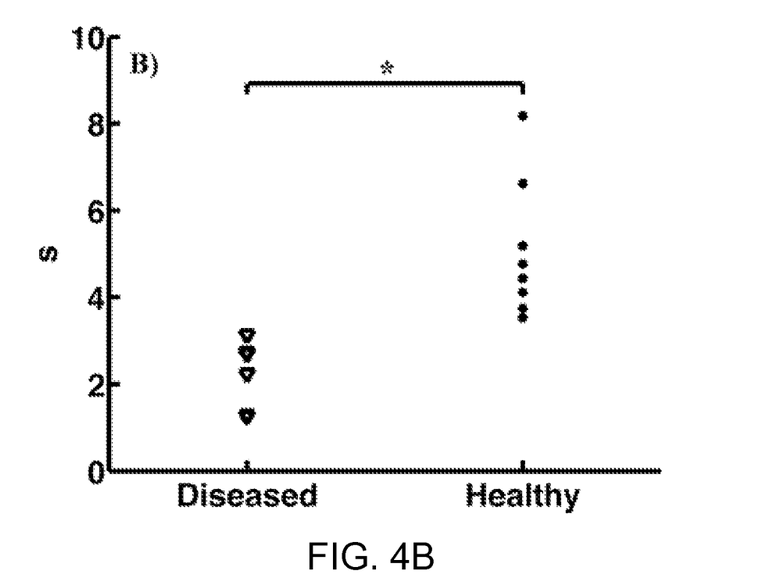
FIG. 4B is a chart illustrating values of s from all Healthy and Diseased patients of FIG. 4A.

In order to determine whether feedback is present in the Healthy and Diseased patients, we separately calculated the $n^{th}$ TR ($TR_n$) and RT ($RT_n$) intervals from the entire ECG data set, corresponding to $DI_n$ and $APD_n$, respectively, as indicated in FIG. 1. Therefore, the relationship between TR and RT intervals correlates with the relationship between DI and APD, i.e. feedback. FIG. 4A shows representative examples of the $n^{th}$ RT intervals as a function of the $n^{th}$ TR intervals for two Healthy (open and filled circles) and two Diseased (open and filled triangles) patients. Note that for Healthy patients, the standard deviations of the TR range are higher than in the RT range, while for Diseased patients the standard deviations for both ranges are similar. To quantify this data, we calculated the sensitivity, s, according to Eq. (5), which is an indirect representation of feedback (see FIG. 4B). Note that s was significantly higher for Healthy patients (s=5.1±0.6) than for Diseased patients (s=2.2±0.3, p<0.01), suggesting the presence of different associations between RT and TR intervals for Healthy than for Diseased patients.

3. The Effect of HRV on Alternans Formation in the Presence of Feedback

Figure 5A:
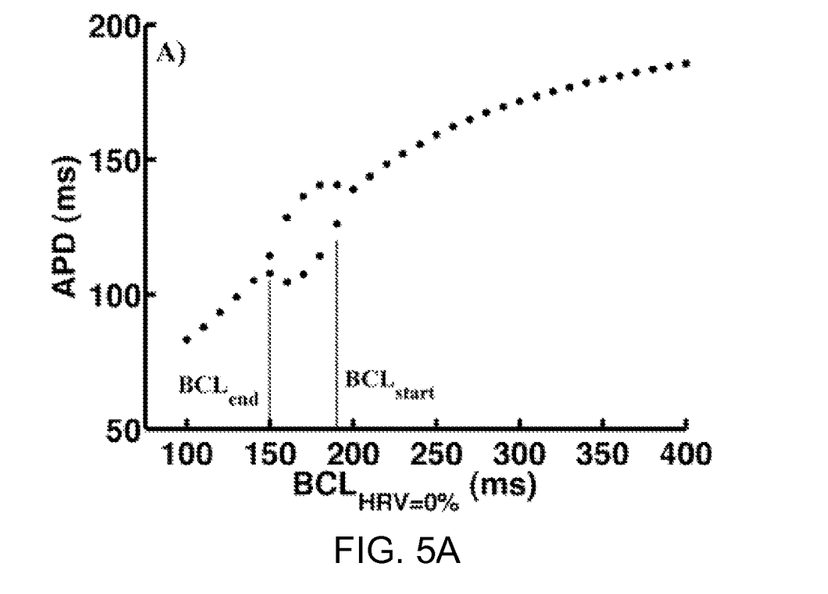
FIGS. 5A and 5B are charts illustrating APD as a function of BCL for an ionic model paced in accordance with embodiments of Protocol 1 with HRV=0% and 2.5%, respectively.
Figure 5B:
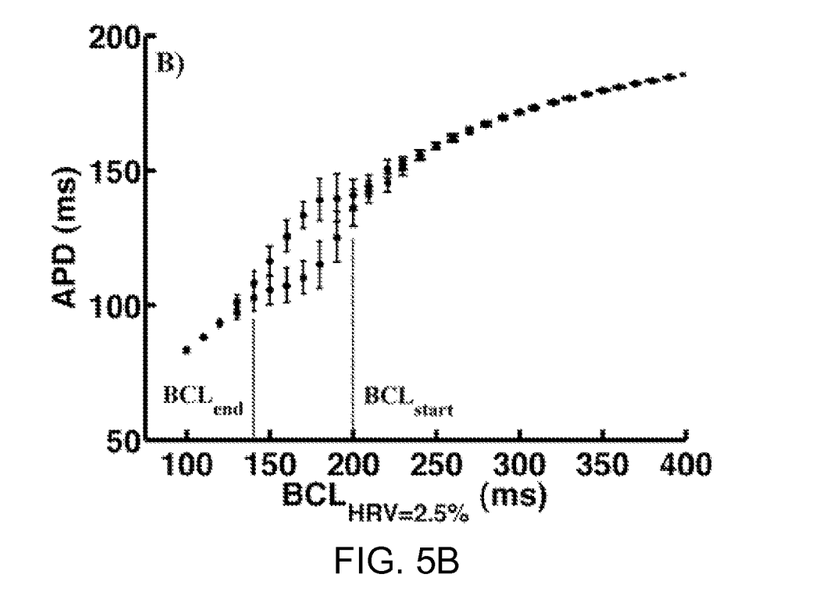

FIG. 5 shows APD as a function of BCL for the ionic model of an isolated cardiac myocyte that was paced using the periodic pacing protocol (Protocol 1) with no HRV (FIG. 5A) and HRV=2.5% (FIG. 5B). $BCL_{start}$ and $BCL_{end}$ denote the start and end of APD alternans. Note the formation of alternans at a certain range of BCLs both with and without HRV. Also note that the onset of alternans occurred at a higher BCL ($BCL_{start}$=200 ms) and ended at a lower BCL ($BCL_{end}$=140 ms) for HRV=2.5% than for HRV=0% ($BCL_{start}$=190 ms and $BCL_{end}$=150 ms, respectively).

Figure 6A:
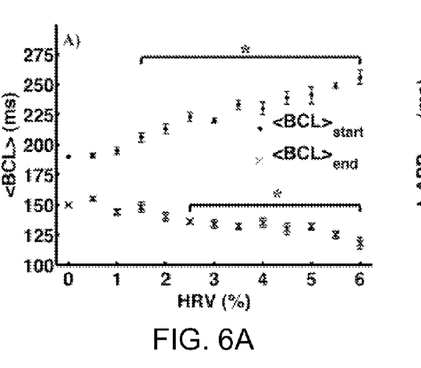
FIGS. 6A-D are charts illustrating the influence of HRV on the following parameters: $<BCL>_{start}$ and $<BCL>_{end}$ (FIG. 6A); $\Delta APD_{max}$ (FIG. 6B); $\Delta APD_{BCL=170\ ms}$ (FIG. 6C); and $<S_r^{max}>$ (FIG. 6D).

FIG. 6A illustrates the influence of HRV on the onset, $<BCL>_{start}$, and the end, $<BCL>_{end}$, of alternans. As HRV is increased, alternans occurred earlier in the pacing protocol and ended later in the pacing protocol. Note that HRV larger than 1.5% significantly increases $<BCL>_{start}$ when compared to HRV=0%. Similarly, HRV larger than 2.5% significantly decreases $<BCL>_{end}$. These results suggest that HRV promotes the formation of alternans for the case of Protocol 1 with feedback.

Figure 6B:
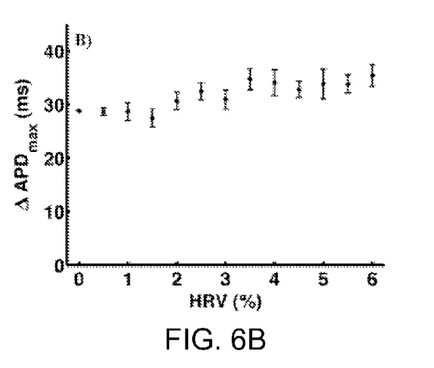
Figure 6C:
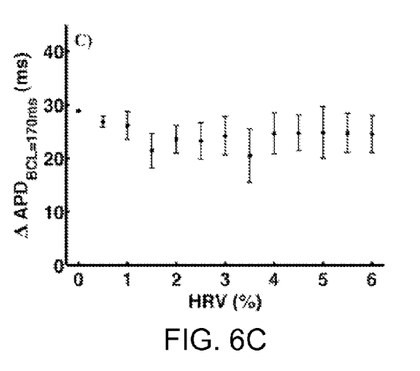

In order to investigate the effect of HRV on the amplitude of alternans, we calculated two parameters: the maximal amplitude of alternans, $\Delta APD_{max}$, over all BCLs in the run and the amplitude of alternans at BCL=170 ms, $\Delta APD_{BCL=170\ ms}$, where alternans was present at HRV=0%. The influence of HRV on $\Delta APD_{max}$ and $\Delta APD_{BCL=170ms}$ is shown in FIGS. 6B and 6C, respectively. FIGS. 6B and 6C shows that the presence of HRV did not significantly affect either $\Delta APD_{max}$ or $\Delta APD_{BCL=170\ ms}$ when compared to values at HRV=0%.

Figure 6D:
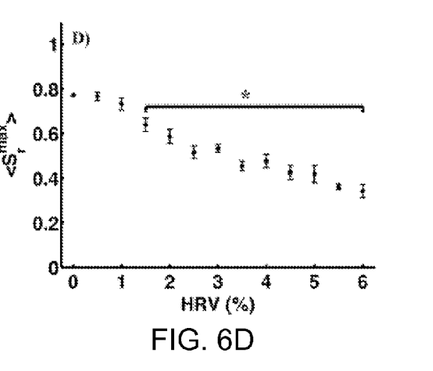

To further understand the effect of HRV on the onset of alternans in the presence of feedback, we calculated the maximum slope of the restitution curve, $<S_r^{max}>$, at the onset of alternans, $<BCL>_{start}$. FIG. 6D shows that HRV≥1.5% leads to a significant decrease of $<S_r^{max}>$ when compared to HRV=0%.

4. Elimination of Feedback Suppresses the Formation of Alternans

Figure 7A:
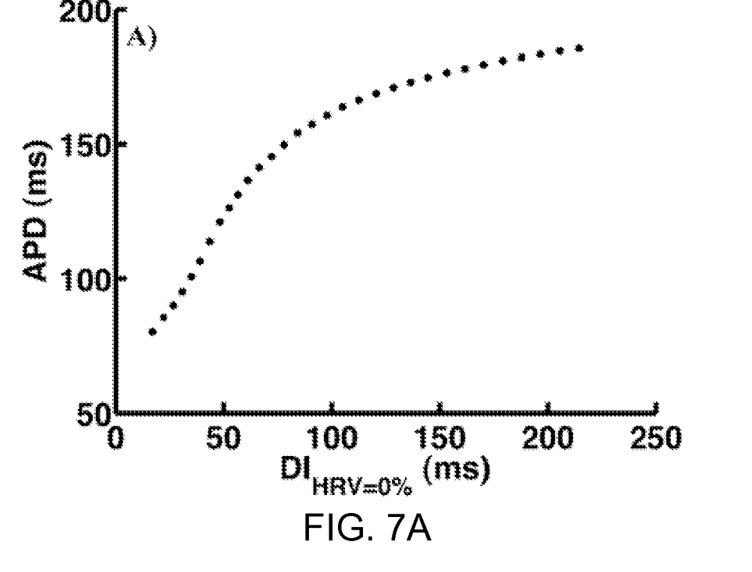
FIGS. 7A and 7B are charts illustrating APD as a function of DI for an ionic model paced in accordance with embodiments of Protocol 2 with HRV=0% and 2.5%, respectively.
Figure 7B:
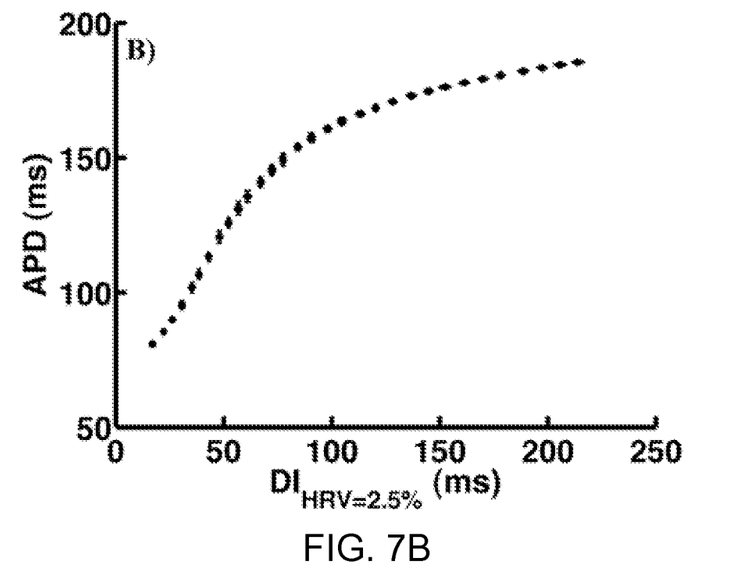

FIG. 7 shows APD as a function of DI for the ionic model of an isolated cardiac myocyte that was paced using Protocol 2 without feedback with HRV=0% (FIG. 7A) and HRV=2.5% (FIG. 7B). Note that in contrast to FIG. 5, no alternans is seen in FIG. 7 (confirmed by inspection of actual voltage traces) both for HRV=0% or 2.5%. To confirm these findings, we increased HRV up to 12%, and alternans was still absent (data not shown). This demonstrated that elimination of feedback prevents formation of alternans in a myocyte.

Figure 8A:
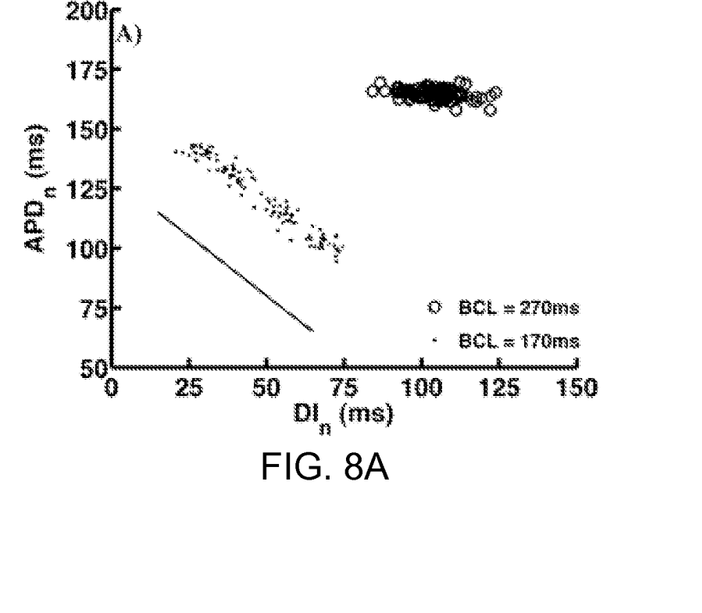
FIG. 8A is a chart illustrating feedback represented via $APD_n$ as a function of the $DI_n$ for Protocol 1 with HRV=2.5% at BCL=270 ms (open circles) and BCL=170 ms (filled circles).
Figure 8B:
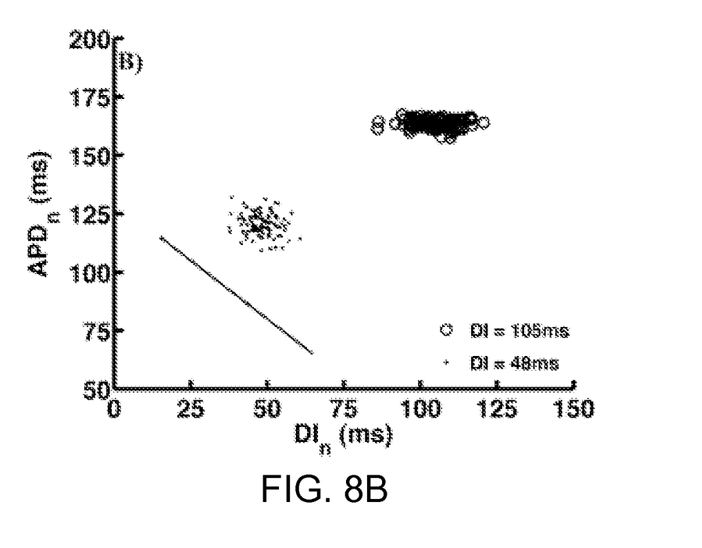
FIG. 8B is a chart illustrating feedback represented via $APD_n$ as a function of the $DI_n$ for Protocol 2 with HRV=5%, shown for the DI=105 ms (open circles) and DI=48 ms (filled circles).

FIG. 8 illustrates the presence of feedback in a cardiac myocyte that was paced either with Protocol 1 (FIG. 8A) or Protocol 2 (FIG. 8B).

Specifically, in FIG. 8A, $APD_n$ is plotted as a function of $DI_n$ for Protocol 1 with HRV=2.5%. To demonstrate the presence of feedback for different BCLs, two values of BCLs were chosen: BCL=270 ms (open circles), and BCL=170 ms (filled circles). In the case of HRV=2.5%, Protocol 1 led to steady state 1:1 responses at BCL=270 ms, and alternans at BCL=170 ms. FIG. 8A suggests that the distribution of data for BCL=270 ms was qualitatively similar to the data from Healthy patients (see FIG. 4A). However, it is important to note that the ranges of the values were very different, thus preventing us from making any distinct conclusions. On the other hand, for BCL=170 ms, the $DI_n$ and $APD_n$ pairs fall along a line with slope of −1, as predicted by Eq. (2).

Similar simulations were performed with Protocol 2, and the results are shown in FIG. 8B. Here two values of DI were chosen, DI=48 ms (open circles) and DI=105 ms (filled circles), as these DI values correspond to the steady state BCLs 170 ms and 270 ms, respectively. FIG. 8B demonstrates that for DI=105 ms the distribution of the $DI_n$ and $APD_n$ was qualitatively similar to the one from Healthy patients (see FIG. 4A). On the other hand, for DI=48 ms the feedback was qualitatively similar to the one from Diseased patients (see FIG. 4A). However, this observation does not allow us to make any distinct conclusions since the ranges of values were very different.

Overview of Inventive Discoveries

The foregoing investigation into the effects of HRV and feedback on the development of alternans in a physiological ionic model of a canine cardiac action potential demonstrates that HRV promoted the formation of alternans in cardiac myocytes in the presence of feedback. Specifically HRV >1.5% significantly shifted the onset of alternans towards larger BCL, but does not affect the amplitude of alternans, $\Delta APD_{max}$ and $\Delta APD_{BCL=170ms}$. This shift of the onset of alternans was accompanied by a significant decrease in $<S_r^{max}>$ value for the same HRV values. Additionally, the absence of feedback during pacing prevented the formation of alternans in cardiac myocytes regardless of the presence or absence of HRV. Since alternans is closely correlated with arrhythmias, prevention of alternans formation is an important area of research in cardiac electrophysiology.

In the case of periodic pacing protocol with feedback, HRV facilitated alternans formation in isolated cell. Indeed, FIG. 5A shows that the introduction of HRV causes <BCL>start to occur at larger values and <BCL>end to occur at lower values, suggesting a potential pro-arrhythmic effect of HRV. Interestingly, the increased range of BCL for which alternans was observed was accompanied by a decreased $<S_r^{max}>$ value at the onset of alternans, suggesting that alternans can be formed in the absence of steep restitution slope, thus again confirming a potential pro-arrhythmic effect of HRV.

Removing the feedback from the pacing protocol (Protocol 2) resulted in the elimination of alternans in isolated cardiac cells. Moreover, alternans did not appear when HRV was introduced in that case, indicating a potential anti-arrhythmic role of no-feedback pacing.

In the investigation described above, HRV was modeled with a random number function, and an assumption was made that HRV does not change as the heart rate changes. This is an over-simplified approach. Indeed, it is known that HRV can be affected by, but not limited to, respiration, thermoregulation, hormonal regulation, blood pressure, etc. In addition, the relative contribution and importance of all these physiological aspects of HRV might be altered under different disease conditions.

Exemplary Embodiments of the Invention

Figure 9:
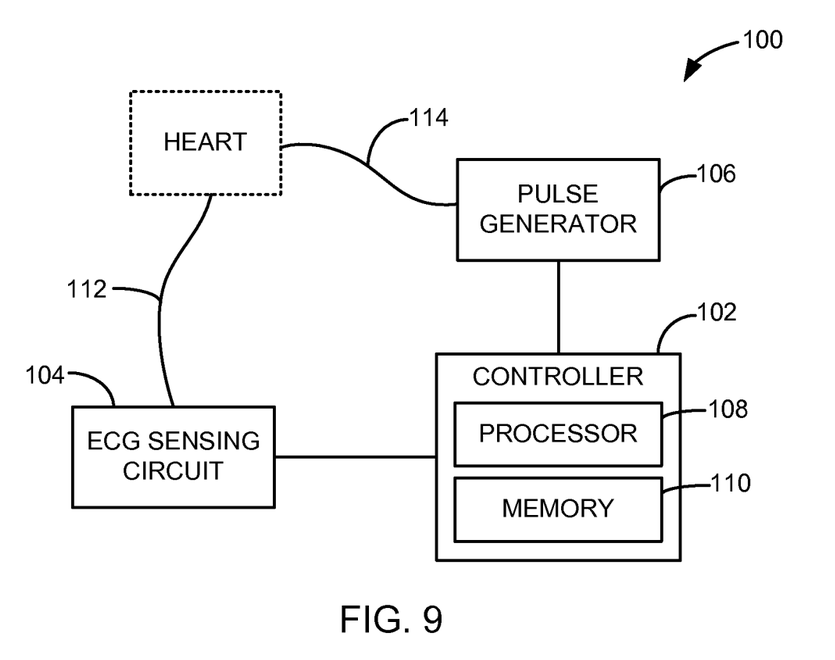
FIG. 9 is a block diagram of an exemplary heart monitoring an pacing device in accordance with embodiments of the invention.

In general, embodiments of the invention include the application of the alternans prevention pacing protocol (Protocol 2) described above to the heart of a human patient to prevent the formation of alternans or, in the event that alternans has begun to form, eliminating the alternans and preventing their subsequent formation. FIG. 9 is a block diagram of an exemplary heart monitoring an pacing device 100 in accordance with embodiments of the invention that may be used to perform the pacing protocol, functions and methods described herein. In some embodiments, the device 100 is an implantable device, such as a pacemaker, or a device or system having both implanted components and components that are external to the patient, or other suitable device.

In some embodiments, the device 100 includes a controller 102, an electrocardiogram (ECG) sensing circuit 104 and/or a pulse generator 106. In some embodiments, where the analysis of ECG traces is not required, the ECG sensing circuit represents a heart rate monitoring unit. The controller 102 includes at least one processor 108. In some embodiments, the controller 102 includes memory 110. In some embodiments, the processor 108 is configured to execute instructions stored in the memory 110 to perform functions and method steps described herein.

The ECG sensing circuit 104 may operate in accordance with conventional circuits that are used to sense ECG signals of the heart of the patient. In some embodiments, the ECG sensing circuit 104 is configured to detect ECG signals of the heart of the patient through one or more leads 112, or other suitable channel. The sensed ECG signals may be converted into data (i.e., ECG trace data) that may be analyzed by the controller 102.

The controller 102 is configured to analyze the ECG signals or trace data using the processor 108. In some embodiments, this analysis involves determining a heart rate (RR period), the RT period, the peak of the T-wave, the TR period, and/or other heartbeat related information that may be extracted from the ECG signals or trace data illustrated in FIG. 1.

The pacing protocol implemented by the device 100 generally involves the application of a heart pacing pulse (electrical pulse) to the heart of the patient using the pulse generator 106 in accordance with conventional techniques. In some embodiments, the heart pacing pulse is delivered to the heart of the patient through one or more leads 114 or other channels.

One exemplary objective of embodiments of the invention is to prevent the formation of alternans in the heart of the patient. In some embodiments, this involves commencing the prevention pacing protocol (Protocol 2) prior to the onset of alternans. In some embodiments, the commencement of the prevention pacing protocol (Protocol 2) is triggered when the heart rate of the patient reaches (e.g., meets or exceeds) a threshold value. In some embodiments, the threshold value is empirically determined based on various parameters of the patient, such as, for example, the age of the patient, the weight of the patient, and other factors.

In some embodiments, the heart rate threshold value is a custom setting for the patient. In some embodiments, the heart rate threshold value for the patient may be determined by monitoring the ECG of the patient, such as during exercise, and determining the heart rate at which alternans begins to form or are likely to begin to form. In some embodiments, the heart rate threshold value is set at a rate that is less than the rate at which alternans was found to begin to form.

In some embodiments, the heart rate threshold value is stored in the memory 110, and the controller 102 or processor 108 periodically compares a current heart rate of the patient to the threshold value. When the heart rate of the patient reaches the threshold value, the controller 102 begins the prevention pacing protocol (Protocol 2).

In some embodiments, the alternans prevention pacing protocol may be triggered based on the detection of alternans by the controller 102, and used to terminate the alternans. In some embodiments, the controller 102 can analyze the ECG trace data obtained using the ECG sensing circuit 104 for a predetermined pattern (e.g., stored in the memory 110) indicating the formation of alternans, and commence the prevention pacing protocol (Protocol 2) when the pattern is detected. In some embodiments, the controller 102 analyzes the ECG trace data to detect the potential presence of alternans having a threshold amplitude (e.g., value stored in the memory 110), and commence the prevention pacing protocol (Protocol 2) when alternans having the threshold amplitude are detected.

In some embodiments, the controller 102 compares a targeted TR period for the current heart rate of the patient, which may be stored in the memory 110, to the current TR interval (FIG. 1). The targeted TR period generally defines a normal or acceptable TR interval for the given heart rate. In some embodiments, the controller commences the alternans prevention pacing protocol (Protocol 2) when the controller 102 determines that the current TR interval deviates from the targeted TR period by a threshold value. The threshold value may be stored in the memory 110 and indexed to a particular heart rate.

In some embodiments, the controller 102 commences the alternans prevention pacing protocol (Protocol 2) when the controller determines that the current TR interval alternates between being longer than the targeted TR period and shorter than the targeted TR period. In some embodiments, the prevention pacing protocol (Protocol 2) is triggered when this alternation of the current TR interval occurs over a threshold number of heartbeats, and/or the deviation of the TR interval from the targeted TR period exceeds a threshold value. The threshold value may be stored in the memory 110 and indexed to a heart rate.

Embodiments of the alternans prevention pacing protocol (Protocol 2) generally involve pacing the heart of the patient to control the TR interval (FIG. 1). In some embodiments, the pacing protocol forces the TR interval of each heartbeat toward a targeted TR period.

In some embodiments, the targeted TR period is a value that is accessible by the controller 102, and is stored in the memory 110 or other suitable location. In some embodiments, the targeted TR period varies based on the heart rate of the patient. Thus, multiple targeted TR periods may be stored in the memory 110 or other location that are each indexed to a heart rate. Here, the controller 102 can acquire the targeted TR period from the memory 110 based on the current heart rate of the patient, which may be an average heart rate taken over a predetermined period of time. In some embodiments, the targeted TR periods are empirically set or are customized for a particular patient. Alternatively, a formula for the targeted TR period based on the heart rate may be stored in the memory 110 or other location, which is accessible by the controller 102. In this case, the current or average heart rate of the patient is used by the controller 102 to calculate the targeted TR period using the formula. The formula may be set empirically or customized to a particular patient.

Once the alternans prevention pacing protocol (Protocol 2) is triggered based on one or more embodiments described above, the targeted TR period is determined by the controller 102. The controller 102 detects the T-wave of an ECG trace of a current heart beat that was retrieved using the ECG sensing circuit 104. The controller 102 then controls the pulse generator 106 to apply a heart pacing pulse at a predetermined interval that is based on the targeted TR period. This process of detecting the T-wave and applying the heart pacing pulse is then repeated for subsequent heartbeats over a limited period of time.

In some embodiments, the predetermined interval is the targeted TR period. This is generally the case when the pacing protocol commences prior to any alternans formation.

In some embodiments, the prevention pacing protocol (Protocol 2) is triggered shortly after alternans has been detected. Here, the RT period and the TR period vary from beat to beat. As a result, it is desirable to attempt to force the TR interval to the targeted TR period using pacing.

In some embodiments, after the onset of alternans, the controller 102 determines an initial TR interval for an initial heartbeat using the trace data obtained using the ECG sensing circuit 104. During the subsequent heartbeat, the controller 102 detects the T-wave using the trace data obtained using the ECG sensing circuit 104, and applies a heart pacing pulse to set the TR interval based on the initial TR interval. In some embodiments, the set TR interval is substantially the same as the initial TR interval. Thus, while the TR interval in the subsequent heartbeat would have changed due to the alternans, the pacing protocol in accordance with embodiments of the invention substantially prevents this change from occurring. The controller 102 continues to apply the heart pacing pulses for subsequent beats to terminate the alternans and prevent further alternans formation, for a limited period of time.

Since the RT interval for the subsequent heartbeat is different from that of the first heartbeat due to alternans, the RR interval changes in the subsequent heartbeat. In some embodiments, this change is reduced from beat-to-beat by gradually adjusting the set TR interval toward the targeted TR interval, which may be based on an average heart rate that was measured prior to the commencement of the pacing protocol. The rate at which the set TR interval is adjusted may be set empirically or be patient dependent. Once the set TR interval reaches the targeted TR period, the alternans prevention pacing protocol may continue pacing the heart to maintain the targeted TR period for a limited period of time.

In some embodiments, the alternans prevention pacing protocol (Protocol 2) does not restrict the heart rate or RR period. That is, the RR period may adjust in response to the needs of the patient while the alternans prevention pacing protocol is being implemented by the device 100. Thus, the pacing protocol in accordance with embodiments of the invention does not prevent the heart rate of the patient from rising or falling. In some embodiments, the controller 102 adjusts the targeted TR period in response to changes in the heart rate of the patient.

In all embodiments described above, HRV might be included at any time when controlling TR interval. HRV can be measured from the patient's ECG or can be set manually. Inclusion of HRV at any physiological values will not affect the outcomes of alternans prevention pacing protocol.

Although the present invention has been described with reference to preferred embodiments, workers skilled in the art will recognize that changes may be made in form and detail without departing from the spirit and scope of the invention.

What is claimed is:

1. A method of preventing the formation of alternans in the heart of a patient using a heart monitoring and pacing device that includes a processor, memory, an electrocardiogram (ECG) sensing circuit, and a pulse generator, the method comprising:
   detecting a heartbeat rate of the heart using a lead, the ECG sensing circuit and the processor;
   determining that the detected heartbeat rate has reached a threshold value stored in the memory using the processor;
   pacing the heart to force the TR period of a limited number of heartbeats toward a targeted TR period, which is stored in the memory, using the pulse generator.

2. The method according to claim 1, further comprising implanting the device in the patient.

3. The method according to claim 1, further comprising extracting the targeted TR period from the memory based on the heartbeat rate using the processor.

4. A method of terminating alternans in a heart of a patient using a heart monitoring and pacing device that includes a processor, memory, an electrocardiogram (ECG) sensing circuit, and a pulse generator, the method comprising:
   sensing electrocardiogram (ECG) signals through at least one lead;
   detecting alternans in the heart comprising analyzing ECG traces corresponding to a plurality of heartbeats using the ECG sensing circuit and the processor based on the sensed ECG signals; and
   controlling the TR period of a limited number of heartbeats comprising applying heart pacing pulses to the heart at a forced TR period using the pulse generator.

5. The method according to claim 4, wherein:
   the method comprises detecting a current TR period of a heartbeat using the ECG sensing circuit and the processor prior to controlling the TR period; and
   setting the forced TR period based on the current TR period using the processor.

6. The method according to claim 4, wherein the forced TR period is set using the processor based on a heartbeat rate of the heart.

7. The method according to claim 4, comprising retrieving the forced TR period from the memory using the processor.

8. The method according claim 4, further comprising adjusting the forced TR period during controlling the TR period.

9. The method according to claim 8, wherein adjusting the forced TR period comprises adjusting the forced TR period toward a target TR period, which is based on the heartbeat rate.

10. The method according to claim 4, wherein detecting alternans in the heart comprises:
    detecting a heartbeat rate of the heart using the processor; and determining that the detected heartbeat rate has reached a threshold value stored in the memory using the processor.

11. The method according to claim 4, wherein detecting alternans in the heart comprises detecting a beat-to-beat variance in the RT period or the TR period using the ECG traces and the processor.

12. The method according to claim 4, wherein detecting alternans in the heart comprises detecting a predetermined pattern in the ECG traces using the processor.

13. The method according to claim 12, wherein detecting alternans in the heart comprises detecting that a threshold number of the heartbeats alternate between having a TR period that is longer than a targeted TR period by a threshold amount, and/or having a TR period that is shorter than the targeted TR period by a threshold amount, using the ECG traces and the processor.

14. The method according to claim 13, wherein the targeted TR period is based on a heartbeat rate of the heartbeats.

15. The method according to claim 4, wherein detecting alternans in the heart comprises detecting alternans in the ECG traces having a threshold amplitude using the processor.

16. An implantable medical device for preventing or terminating alternans in a heart of a patient, the device comprising:
    at least one lead;
    memory containing a mapping of target TR periods to heartbeat rates;
    an electrocardiogram (ECG) sensing circuit configured to generate ECG trace data based on ECG signals sensed through the at least one lead;
    a pulse generator configured to deliver heart pacing pulses through the at least one lead; and
    a controller comprising at least one processor configured to execute program instructions stored in the memory to prevent the formation of alternans in the heart or to terminate alternans in the heart using the target TR periods, the ECG sensing circuit, the pulse generator and the at least one lead.

* * * * *